US00PP27864P2

(12) United States Plant Patent
Bédard

(10) Patent No.: US PP27,864 P2
(45) Date of Patent: Apr. 11, 2017

(54) GROUND COVER ROSE PLANT NAMED 'WEKSUSACOFLOC'

(50) Latin Name: *Rosa hybrida*
Varietal Denomination: WEKsusacofloc

(71) Applicant: Early Morning LLC, Pomona, CA (US)

(72) Inventor: Christian Bédard, Placentia, CA (US)

(73) Assignee: Early Morning LLC, Pomona, CA (US)

( * ) Notice: Subject to any disclaimer, the term of this patent is extended or adjusted under 35 U.S.C. 154(b) by 0 days.

(21) Appl. No.: 14/757,090

(22) Filed: Nov. 16, 2015

(51) Int. Cl.
*A01H 5/02* (2006.01)

(52) U.S. Cl.
USPC ..... Plt./104

(58) Field of Classification Search
USPC ..... Plt./104
See application file for complete search history.

(56) References Cited

U.S. PATENT DOCUMENTS

PP10,240 P 2/1998 Ilsink

*Primary Examiner* — Annette Para
(74) *Attorney, Agent, or Firm* — McKee, Voorhees & Sease, PLC

(57) ABSTRACT

A new variety of Ground Cover rose suitable for garden decoration, having flowers of medium yellow to buttery gold coloration.

1 Drawing Sheet

Classification: The present invention relates to a new *Rosa hybrida* plant.

Variety denomination: The new plant has the varietal denomination 'WEKsusacofloc'.

BACKGROUND OF THE INVENTION

This invention relates to a new and distinct variety of Ground Cover Rose. It has as its seed parent the variety known as 'INTerdust' (U.S. Plant Pat. No. 10,240) and a non-disseminated seedling of my creation as its pollen parent with the following genetic origin City of San Francisco×(Neon Cowboy×Flower Carpet).

SUMMARY OF THE INVENTION

Among the features which distinguish the new variety from other presently available and commercial rose cultivars known to the inventor are the following combinations of characteristics: its low spreading growing habit, its excellent color stability throughout the life of the flower and its many hairs on the edges of the grooves on the upper side of the rachis. The plant has a low spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKsusacofloc' may be asexually propagated by cuttings, budding and grafting. The budding and grafting successfully occurred on the plant/rootstock *Rosa hybrida* cv. "Dr. Huey" (not patented).

COMPARISON WITH PARENTS

The new rose may be distinguished from its seed parent, 'INTerdust' by the following combination of characteristics:

whereas 'WEKsusacofloc' bears medium sized flowers (about 4.4 to about 5.6 cm. in diameter) of medium yellow to buttery gold coloration, 'INTerdust' bears significantly smaller flowers (about 3.8 cm. in diameter) of light yellow coloration. The new variety bears double flowers (about 14 to 32 petals), whereas the seed parent bears single to semi-double flowers with significantly lesser petalage (about 5 to 10 petals).

The new variety may be distinguished from its pollen parent, a non-disseminated seedling of my creation by the following combination of characteristics: whereas 'WEKsusacofloc' bears medium sized flowers (about 4.4 to about 5.6 cm. in diameter) of medium yellow to buttery gold coloration, the non-disseminated seedling bears significantly larger flowers (about 6.0 to about 7.5 cm. in diameter) of medium red coloration with a yellow eye zone. The new variety bears double flowers (about 14 to 32 petals), whereas the pollen parent bears semi-double flowers with significantly lesser petalage (about 8 to 12 petals).

COMPARISON WITH THE CLOSEST COMMERCIALLY AVAILABLE CULTIVAR

The closest commercially available cultivar to the new variety is the seed parent 'INTerdust' (U.S. Plant Pat. No. 10,240).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of November.

Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety sometimes bears its flowers singly, usually in clusters of three to nine or more per stem. Flowers are borne in regular rounded to somewhat pyramidal clusters on strong short to medium length stems (about 23 to about 70 cm.). The cluster ranges from about 7.9 to about 13.3 cm. in diameter. Outdoors, the plant blooms abundantly and nearly continuously during the growing season. The flowers have a moderate fruity fragrance.

BUD

The peduncle is about 1.5 to about 3.1 cm. in length, of slender caliper (about 0.15 to about 0.2 cm. in diameter), and usually erect to somewhat stiff. It is smooth, with very few stipitate glands and some hairs. Peduncle color is between 146C and 148A often lightly suffused, especially on the side exposed to the sun, with between 187B and 187A.

Before the calyx breaks, the bud is about 0.7 to about 1.2 cm. in diameter at the widest point, about 1.1 to about 1.3 cm. in length, and pointed to somewhat ovoid in shape. The surface of the bud bears between 5 to 7 foliaceous appendages with few stipitate glands and some hairs, usually with slender entire foliaceous parts extending beyond the tip of the bud about ¼ or more of its length. Bud color is between 146A and 147B often moderately suffused, especially on the side exposed to the sun, with between 187B and 187A.

The sepals are about 1.3 to about 1.9 cm. in length and about 0.4 to about 0.8 cm. in width at the widest point. The outer surface color of the sepal is between 146A and 147B often moderately suffused, especially on the side exposed to the sun, with between 187B and 187A. The outer surface of the sepal is smooth and bears between 0 to 3 foliaceous appendages with few stipitate glands and some hairs. The inner surface color of the sepal is near 146B broadly bordered by near 137B. The inner surface of the sepal is covered with fine wooly tomentum; sepal margins are lined with very few stipitate glands and some hairs.

The receptacle of the flower is of medium length (about 0.4 to about 0.6 cm.) and average in caliper (about 0.4 to about 0.8 cm. in diameter). The receptacle is urn-shaped in form. Its surface is smooth with some hairs and very few stipitate glands and with somewhat thin fleshy walls. The receptacle color is between 137C and 146A often moderately suffused, especially on the side exposed to the sun, with between 187B and 187A.

As the petals open (after the calyx breaks), the bud is about 1.2 to about 1.6 cm. in diameter at the widest point, about 1.3 to about 1.9 cm. in length, and moderately ovoid to somewhat globular in form. The color of the under surfaces of the newly opened petals is between 16B and 15C often moderately suffused mostly on the outermost petals with between 53B and 53C. There is no visible change in coloration at the point where the petal attaches. The color of the upper surfaces of the newly opened petals is between 13A and 15C. There is no visible change in coloration at the point where the petal attaches.

BLOOM

When fully open, the bloom ranges from about 4.4 to about 5.6 cm. in diameter. Petalage is double with about 14 to 32 petals and about 2 to 7 petaloids irregularly arranged. When partially open, the bloom form is moderately globular to cupped, and the petals are loosely spiraled to cupped with petal edges moderately reflexed inward to sometimes somewhat reflexed outward. When fully open, the bloom form is moderately cupped, and the petals are loosely cupped with petal edges moderately reflexed inward to sometimes somewhat reflexed outward.

PETALS

The substance of the petals is somewhat heavy and of medium to somewhat thin thickness, with upper surfaces moderately shiny to somewhat satiny and under surfaces almost matte to slightly shiny. The petals are about 1.5 to about 2.4 cm. in length and about 0.6 to about 2.3 cm. in width at the widest point. Petal margins are entire.

The outer petals are broadly obovate in shape with rounded apices to sometimes slightly mucronate.

The inner petals are broadly oblanceolate in shape with rounded apices to sometimes slightly mucronate.

Petaloids are about 0.9 to about 2.3 cm. in length and about 0.3 to about 0.8 cm. in width at the widest point. Petaloids are irregularly shaped somewhat oblanceolate to subulate with rounded apices.

NEWLY OPENED FLOWER

The under surface color of the outer, intermediate and inner petals is between 10A and 11A sometimes lightly suffused on the outermost petals with near 59C. There is no visible change in coloration at the point where the petal attaches. The upper surface color of the outer, intermediate and inner petals is between 11A and 11B. There is no visible change in coloration at the point where the petal attaches.

The under and upper surface colors of the petaloids are similar in coloration to the upper and under surfaces of the intermediate and inner petals.

The general tonality of the newly opened flower is between 11A and 11B.

THREE-DAY-OLD FLOWER

The under surface color of the outer, intermediate and inner petals is between 10C and 12D sometimes lightly suffused on the outermost petals with near 59C. There is no visible change in coloration at the point where the petal attaches. The upper surface color of the outer, intermediate and inner petals is between 10C and 12D. There is no visible change in coloration at the point where the petal attaches.

The under and upper surface colors of the petaloids are similar in coloration to the upper and under surfaces of the intermediate and inner petals.

The general tonality of the three-day-old flower is between 10C and 12D.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 145) and are arranged regularly about the pistils; a few are mixed with petaloids. The filaments are of medium length (about 0.3 to about 0.9 cm.) most with anthers. Filaments are near 15A in color often heavily suffused at the base with between 53A and 53B. The anthers are somewhat small to medium for the class and all open approximately at the same time. Anther color when immature is near 22A on the external part and near 11D on the internal part. Anther color at maturity is near 161A on the external part and near 200A on the internal part. Pollen is abundant and between 23B and 21A in color.

FEMALE REPRODUCTIVE ORGANS

Pistils vary in number (average about 45). The styles are moderately even, average in length (about 0.4 to about 0.6 cm.), thin in caliper, and loosely bunched. Stigma color is near 8A. Style color is between 150D and 154D often lightly suffused near the top with near 53C. Ovaries are usually all enclosed in the calyx. The ovaries are somewhat small in size and between 159D and 158D in color.

Hips are of moderately short length (about 0.9 to about 1.2 cm.), rounded in form with a flat top and flat base, and between 34A and 42A in color when ripe. The hip surface is smooth with moderately thick fleshy walls. The sepals are moderately permanent and usually straight in shape.

The seeds are irregularly rounded, smooth in texture, approximately 7 to about 19 per hip, about 0.4 to about 0.5 cm. in diameter at the widest point and between 161A and 161B in color.

FOLIAGE

The compound leaves are usually comprised of three to seven leaflets and are borne abundantly. The five-leaflet leaves are about 4.3 to about 11.0 cm. in length and about 4.5 to about 7.0 cm. in width at the widest point, leathery in texture on both sides, and glossy in finish on the upper side and slightly glossy in finish on the underside. The leaves have a pinnate venation pattern. The terminal leaflets are about 2.2 to about 3.8 cm. in length and about 1.3 to about 2.6 cm. in width at the widest point, shaped ovate with acuminate apices and rounded bases. Their margins are usually simply serrate.

The upper surface color of the mature leaf is between 139A and 147A. The under surface color of the mature leaf is between 137B and 147B. The under and upper colors of the leaf veins on the mature leaf are similar in coloration to the upper and under surfaces colors of the mature leaf. The upper surface color of the young leaf is between 137B and 146A, often heavily suffused with between 187A and 187B. The under surface color of the young leaf is between 137C and 147B, often heavily suffused with between 187A and 187B. The under and upper colors of the leaf veins on the young leaf are similar in coloration to the upper and under surfaces colors of the young leaf.

The rachis is somewhat light in caliper and rough. The upper side is deeply grooved with many hairs and very few stipitate glands on the edges of the grooves. The under side of the rachis is rough with few hairs and stipitate glands and few small prickles. The rachis color is near 146C on the under side and near 137A on the upper side, often heavily suffused on the young leaves with between 187A and 187B.

The stipules are about 0.9 to about 1.6 cm. in length and of medium width (about 0.3 to about 0.5 cm.) with medium to somewhat long straight points that usually turn out at an angle of more than 45 degrees and sometimes recurve toward the stem. The under and upper surface color of the stipule is between 137C and 146B.

The petiole is somewhat light in caliper and rough. The upper side is deeply grooved with many hairs and very few stipitate glands on the edges of the grooves. The under side of the petiole is rough with few hairs and stipitate glands and few small prickles. The petiole is about 1.0 to about 1.8 cm. in length and about 0.1 cm in width at the widest point. The petiole color is near 146C on the underside and near 137A on the upper side, often heavily suffused on the young leaves with between 187A and 187B.

The plant displays an above average degree of resistance to powdery mildew (*Sphaerotheca pannosa*) and rust (*Phragmidium* sp.) as compared to other commercial varieties grown under comparable conditions in Pomona, Calif. The plant's winter hardiness and drought/heat tolerance are yet to be determined.

GROWTH

The plant has a spreading low growing habit (about 45 to about 68 cm. in height and about 180 to about 200 cm. spread at the widest point), with very full branching. It displays vigorous growth and the canes are of medium caliper for the class (about 1.3 to about 1.8 cm. in diameter at the widest point).

The color of the major stems is between 147B and 137B. The major stems are rough in texture and they bear some large prickles that are about 0.6 to about 1.0 cm. in length. The large prickles are moderately angled to somewhat hooked downward with a medium length broad oval base; prickle color is near 165A often heavily suffused with between 201A and 201B. The major stem bears very few small prickles of similar shape and coloration.

The color of the branches is between 146B and 147B. The branches are rough in texture and they bear few large prickles which are of similar shape to the large prickles on the major stems. The prickles are about 0.3 to about 0.4 cm. in length. The prickle color is near 152B sometimes lightly suffused with near 187C. The branches bear very few small prickles of similar shape and coloration.

The color of the new shoots is between 146B and 147B often heavily suffused with between 187B and 187A. The new shoots are rough in texture and they bear few large prickles which are of similar size and shape to the large prickles on the branches; prickle color is between 153A and 152C often heavily suffused with between 187B and 187C. The shoots bear very few small prickles of similar shape and coloration.

I claim:

1. A new and distinct Ground Cover rose plant of the variety substantially as described and illustrated herein.

* * * * *

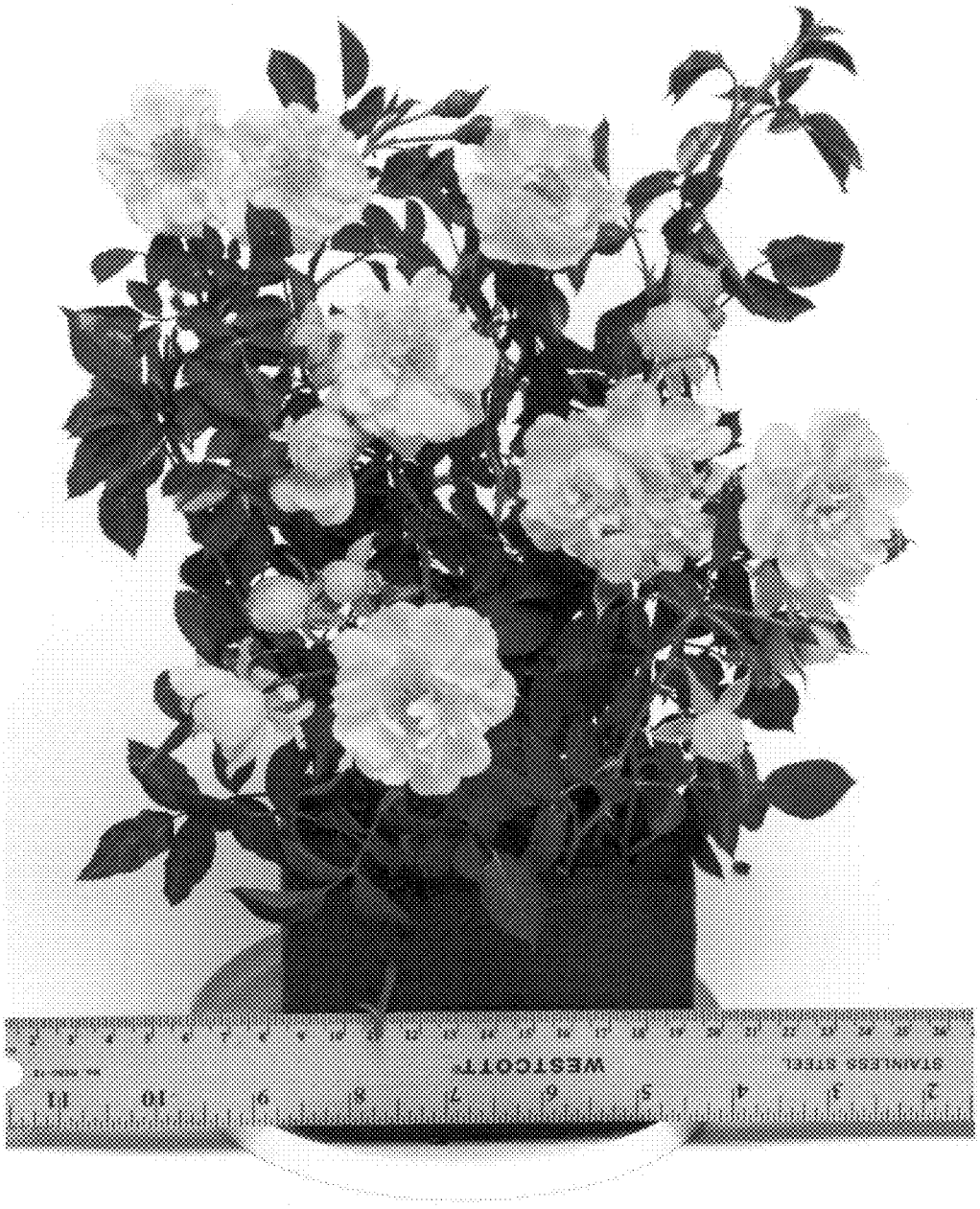
WESTCOTT
STAINLESS STEEL